United States Patent
Skujins et al.

(10) Patent No.: US 7,153,277 B2
(45) Date of Patent: Dec. 26, 2006

(54) COMPOSITE MEDICAL DEVICE WITH MARKERS

(75) Inventors: Peter Skujins, Minneapolis, MN (US); Brian R. Reynolds, Ramsey, MN (US)

(73) Assignee: Scimed Life Systems, Inc., Maple Grove, MN (US)

( * ) Notice: Subject to any disclaimer, the term of this patent is extended or adjusted under 35 U.S.C. 154(b) by 147 days.

(21) Appl. No.: 10/309,306

(22) Filed: Dec. 3, 2002

(65) Prior Publication Data
US 2004/0106878 A1 Jun. 3, 2004

(51) Int. Cl.
*A61B 5/00* (2006.01)
*A61M 25/00* (2006.01)

(52) U.S. Cl. ...................................... 600/585
(58) Field of Classification Search ................ 600/585, 600/433–435; 604/523, 533–535
See application file for complete search history.

(56) References Cited

U.S. PATENT DOCUMENTS

| | | |
|---|---|---|
| 4,080,706 A | 3/1978 | Heilman et al. |
| 4,456,017 A | 6/1984 | Miles |
| 4,538,622 A | 9/1985 | Samson et al. |
| 4,763,647 A | 8/1988 | Gambale |
| 4,813,434 A | 3/1989 | Buchbinder et al. |
| 4,846,186 A | 7/1989 | Box et al. |
| 4,884,579 A | 12/1989 | Engelson |
| 4,925,445 A | 5/1990 | Sakamoto et al. |
| 4,984,581 A | 1/1991 | Stice |
| 5,063,935 A | 11/1991 | Gambale |
| 5,069,226 A | 12/1991 | Yamauchi et al. |
| 5,111,829 A | 5/1992 | Alvarez de Toledo |
| 5,144,959 A | 9/1992 | Gambale et al. |
| 5,209,730 A | 5/1993 | Sullivan |
| 5,213,111 A | 5/1993 | Cook et al. |
| 5,230,348 A | 7/1993 | Ishibe et al. |
| 5,238,004 A | 8/1993 | Sahatjian et al. |
| 5,253,653 A | 10/1993 | Daigle et al. |
| 5,273,052 A | 12/1993 | Kraus et al. |
| 5,275,173 A | 1/1994 | Samson et al. |
| 5,299,580 A | 4/1994 | Atkinson et al. |
| 5,312,356 A | 5/1994 | Engelson et al. |
| 5,313,967 A | 5/1994 | Lieber et al. |
| 5,333,620 A | 8/1994 | Moutafis et al. |
| 5,341,818 A | 8/1994 | Abrams et al. |
| 5,345,945 A | 9/1994 | Hodgson et al. |
| 5,353,808 A | 10/1994 | Viera |
| 5,365,943 A | 11/1994 | Jansen |
| 5,368,048 A | 11/1994 | Stoy et al. |
| 5,406,960 A | 4/1995 | Corso, Jr. |
| 5,411,476 A | 5/1995 | Abrams et al. |
| 5,415,178 A * | 5/1995 | Hsi et al. ..................... 600/585 |
| 5,433,200 A | 7/1995 | Fleischhacker, Jr. |
| 5,443,907 A | 8/1995 | Slaikeu et al. |
| 5,452,726 A | 9/1995 | Burmeister et al. |

(Continued)

FOREIGN PATENT DOCUMENTS

WO  WO 01/95794  12/2001

(Continued)

*Primary Examiner*—Max F. Hindenburg
*Assistant Examiner*—Jonathan Foreman
(74) *Attorney, Agent, or Firm*—Crompton, Seager & Tufte, LLC

(57) ABSTRACT

Medical devices and methods of manufacturing medical devices. The medical devices include an elongate member having a proximal portion and a distal portion and a connector assembly disposed adjacent the elongated member to connect the proximal and distal portions, the connector assembly including a radiopaque marker.

29 Claims, 4 Drawing Sheets

U.S. PATENT DOCUMENTS

| | | |
|---|---|---|
| 5,465,732 A | 11/1995 | Abele |
| 5,479,938 A | 1/1996 | Weier |
| 5,606,981 A | 3/1997 | Tartacower et al. |
| 5,637,089 A | 6/1997 | Abrams et al. |
| 5,651,373 A | 7/1997 | Mah |
| 5,695,111 A | 12/1997 | Nanis et al. |
| 5,769,796 A | 6/1998 | Palermo et al. |
| 5,772,609 A | 6/1998 | Nguyen et al. |
| 5,772,641 A | 6/1998 | Wilson |
| 5,776,100 A | 7/1998 | Forman |
| 5,782,776 A | 7/1998 | Hani |
| 5,788,653 A * | 8/1998 | Lorenzo ................ 600/585 |
| 5,797,857 A | 8/1998 | Obitsu |
| 5,820,571 A | 10/1998 | Erades et al. |
| 5,833,631 A | 11/1998 | Nguyen |
| 5,836,892 A | 11/1998 | Lorenzo |
| 5,836,893 A | 11/1998 | Urick |
| 5,980,471 A | 11/1999 | Jafari |
| 5,984,878 A | 11/1999 | Engelson |
| 6,001,068 A | 12/1999 | Uchino et al. |
| 6,039,699 A | 3/2000 | Viera |
| 6,042,553 A | 3/2000 | Solar et al. |
| 6,106,488 A | 8/2000 | Fleming et al. |
| 6,126,650 A * | 10/2000 | Martinez et al. ............ 604/529 |
| 6,139,510 A | 10/2000 | Palermo |
| 6,165,292 A | 12/2000 | Abrams et al. |
| 6,168,571 B1 | 1/2001 | Solar et al. |
| 6,179,788 B1 | 1/2001 | Sullivan |
| 6,183,420 B1 | 2/2001 | Douk et al. |
| 6,234,981 B1 | 5/2001 | Howland |
| 6,248,082 B1 | 6/2001 | Jafari |
| 6,285,903 B1 | 9/2001 | Rosenthal et al. |
| 6,306,105 B1 | 10/2001 | Rooney et al. |
| 6,325,766 B1 * | 12/2001 | Anderson et al. ........... 600/585 |
| 6,352,515 B1 | 3/2002 | Anderson et al. |
| 6,451,026 B1 * | 9/2002 | Biagtan et al. ............. 606/108 |
| 6,500,147 B1 * | 12/2002 | Omaleki et al. ....... 604/103.09 |
| 2003/0069520 A1 | 4/2003 | Skujins et al. |
| 2003/0069521 A1 | 4/2003 | Reynolds et al. |

FOREIGN PATENT DOCUMENTS

| | | |
|---|---|---|
| WO | WO 03/030982 | 4/2003 |
| WO | WO 03/045490 | 6/2003 |

* cited by examiner

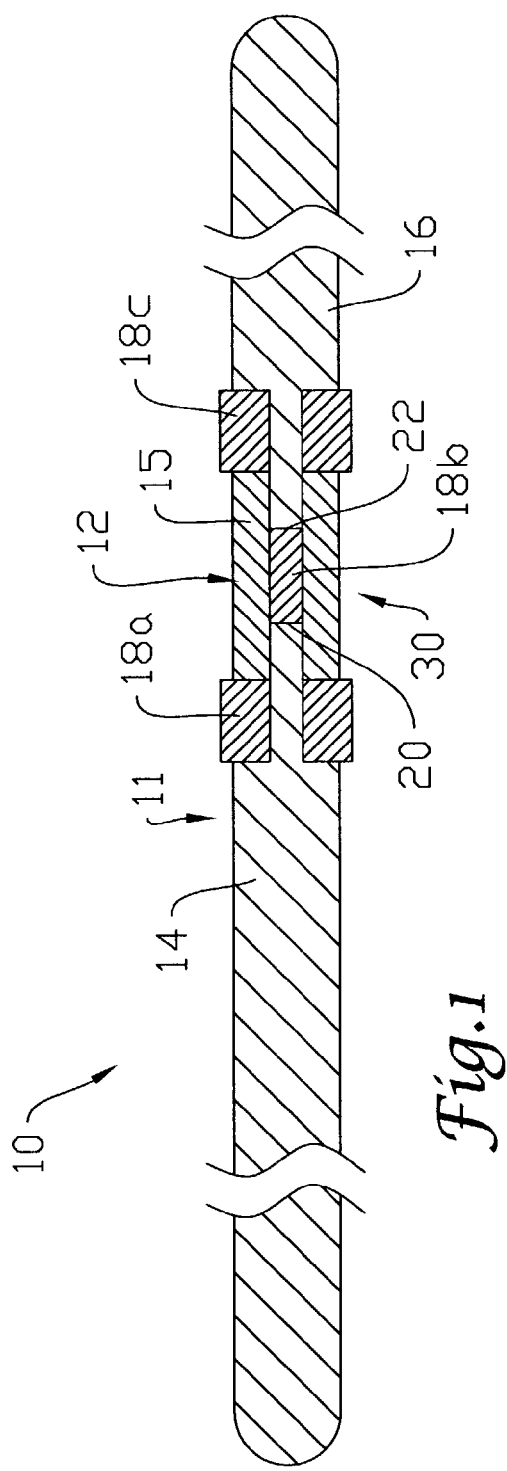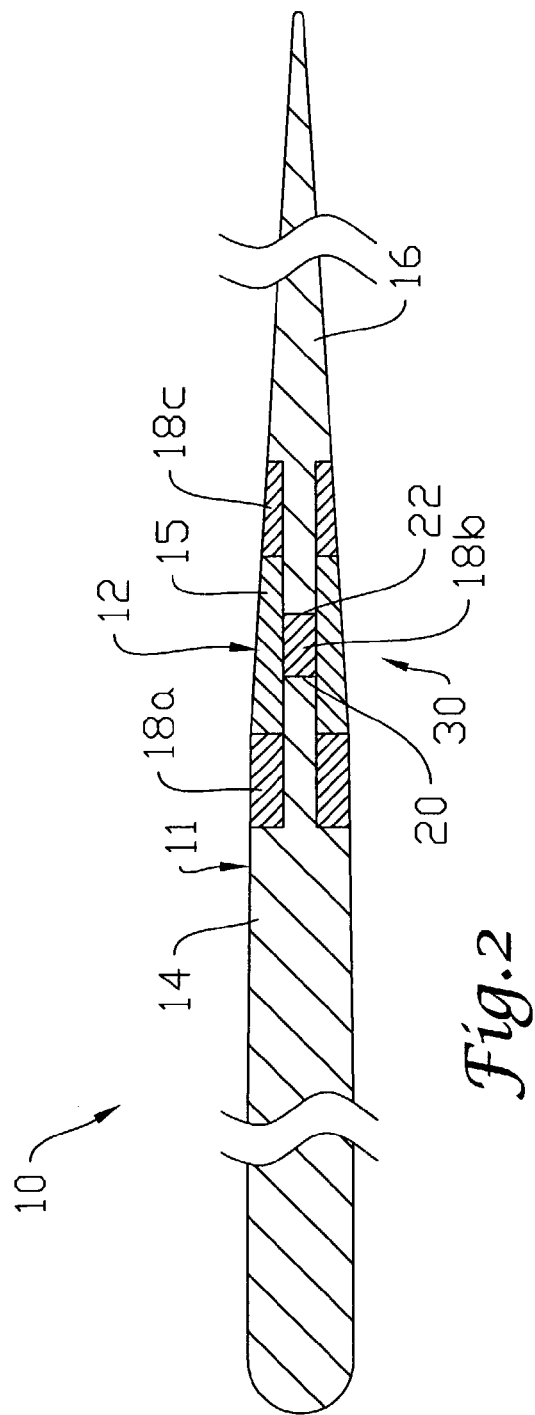

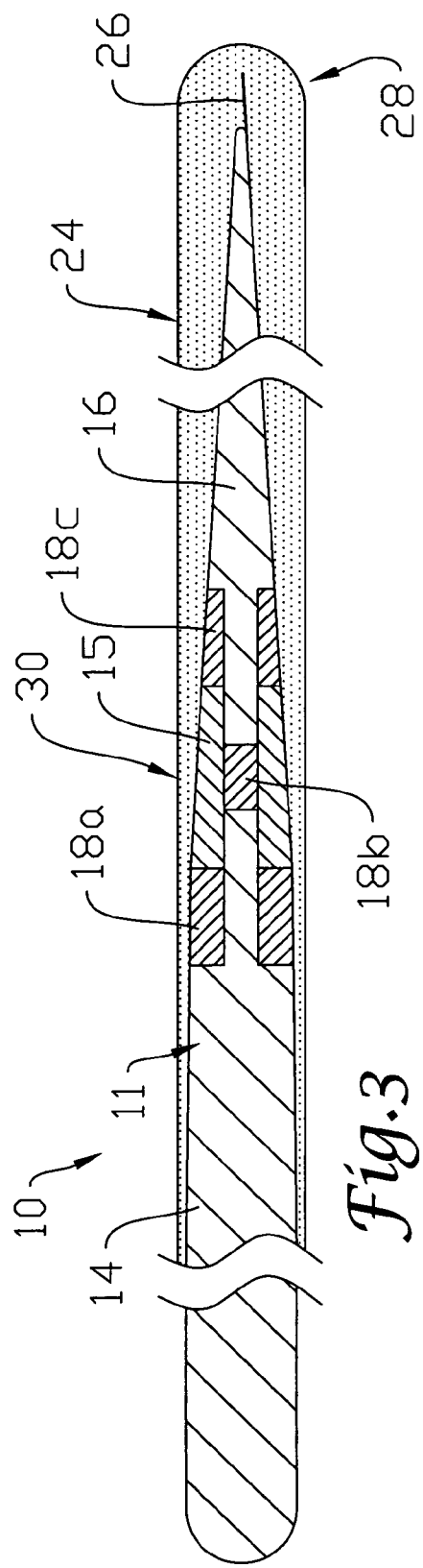
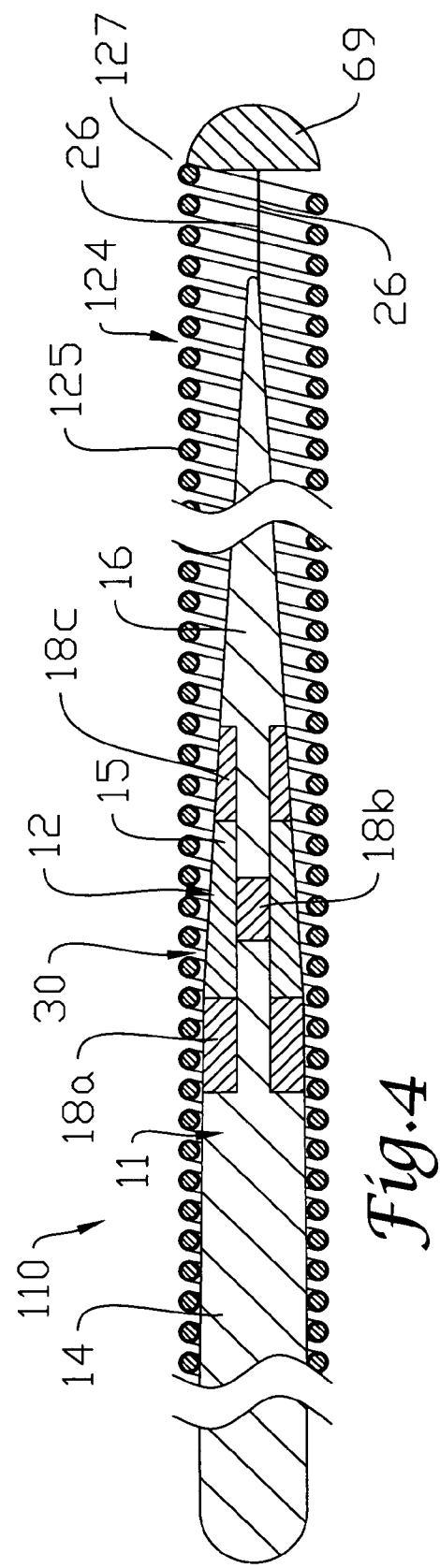

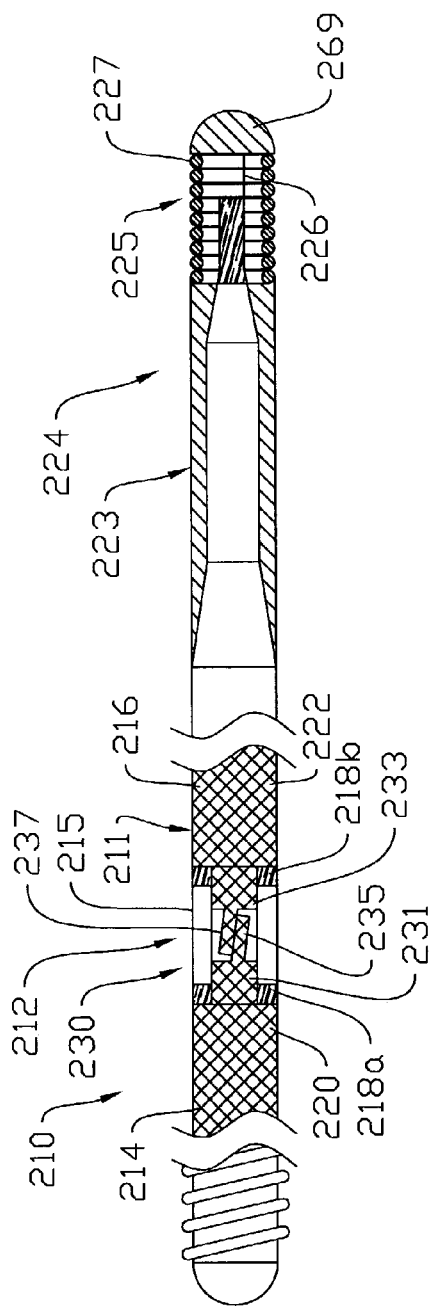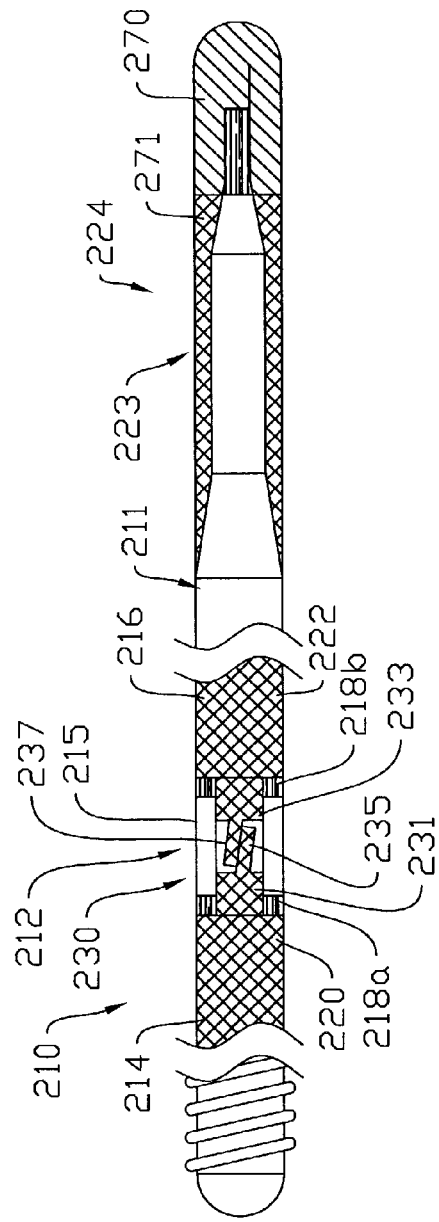

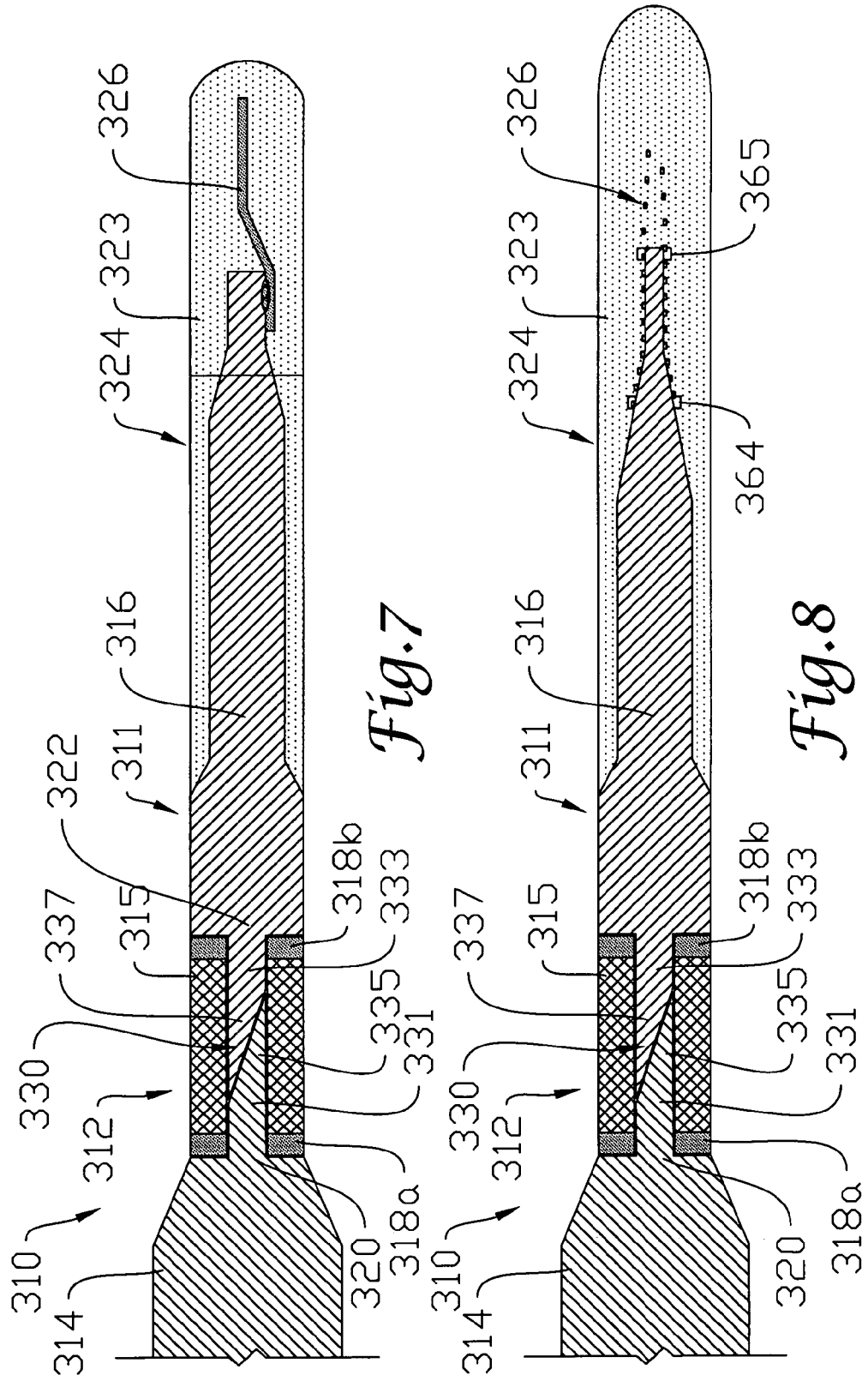

COMPOSITE MEDICAL DEVICE WITH MARKERS

FIELD OF THE INVENTION

The invention pertains to medical devices and, more particularly, to composite medical devices having connector assemblies with structure incorporated therein that is adapted and configured to produce a relatively bright image on a fluoroscopy screen or another imaging technique.

BACKGROUND

A wide variety of medical devices, for example, guidewires and catheters, have been developed for intravascular use. Some such devices are compound or composite devices that include multiple portions coupled together. A number of such different medical devices and assemblies are known, each having certain advantages and disadvantages. There is an ongoing need to provide alternative medical device structures and assemblies.

SUMMARY

The invention provides design, material, and manufacturing method alternatives for medical devices having multiple portions connected together with connecting structure, and including one or more markers that are adapted and configured to produce a relatively bright image on a fluoroscopy screen or another imaging technique used, for example, during a medical procedure. In some embodiments, the markers are included within or adjacent to the connecting structure.

BRIEF DESCRIPTION OF THE DRAWINGS

FIG. 1 is a cross sectional fragmentary view of a guidewire core member (pre-grinding) including a connector assembly for connecting a proximal portion and a distal portion, the connector assembly including radiopaque markers;

FIG. 2 is a cross sectional view of the guidewire core member (post-grinding) of FIG. 1;

FIG. 3 is a cross sectional view of a guidewire including the core member of FIG. 2 and an outer polymeric sleeve attached thereto;

FIG. 4 is a cross sectional view of a guidewire including the core member of FIG. 2 and an outer coil attached thereto;

FIG. 5 is cross sectional view of another embodiment of a guidewire including a guidewire core member having a connector assembly for connecting a proximal portion and a distal portion, the connector assembly including radiopaque markers;

FIG. 6 is a cross sectional view of another embodiment of a guidewire including a guidewire core member and a connector assembly for connecting a proximal portion and a distal portion, the connector assembly including radiopaque markers;

FIG. 7 is a cross sectional view of another embodiment of a guidewire including a guidewire core member and a connector assembly for connecting a proximal portion and a distal portion, the connector assembly including radiopaque markers; and FIG. 8 is a cross sectional view of another embodiment of a guidewire including a guidewire core member and a connector assembly for connecting a proximal portion and a distal portion, the connector assembly including radiopaque markers.

DETAILED DESCRIPTION

In at least some embodiments, the invention relates to a medical device including a first elongated member and a second elongated member connected together using a connector. Each of the elongated portions includes a proximal and a distal end. The connector includes a connector member disposed adjacent the distal portion of the first elongated member and adjacent the proximal portion of the second elongate member to connect the first and second elongated members. One or more markers can be included as part of the connector assembly, are disposed adjacent the connector member, and are useful in imaging the device during use. In at least some embodiments, it is advantageous to incorporate the markers with the connector assembly to enhance ease of construction and in some embodiments, enhance the characteristics of the medical device.

Although set forth with specific reference to guidewires in the example embodiments shown in the Figures and discussed below, the invention may be applicable to almost any medical device having an elongated structure made up of two or more adjacent or consecutive elongated members or sections that are connected together and wherein marker structures would be desirable. For example, the invention may be applicable to elongated shafts, for example hypotube shafts and the like, for intravascular catheters (e.g., guide catheters, diagnostic catheters, rapid exchange balloon catheters, stent delivery catheters, etc.) or drive shafts for intravascular devices (atherectomy catheters, IVUS catheters, intravascular rotational devices, etc.), and the like, or other such medical devices.

The following portions of the description, which describe some example embodiments of the invention, should be read with reference to the drawings, wherein like reference numerals indicate like elements throughout the several views.

FIGS. 1–2 are cross sectional views of an elongated core member 11 of a guidewire 10. The core member 11 includes an elongated proximal portion or member 14, an elongated distal portion or member 16 and a connector structure or assembly 12 that can include any structure or material adapted and configured for connecting the proximal member 14 and the distal member 16. The connector 12 may also include structure or material adapted and configured to produce a relatively bright image on a fluoroscopy screen or another imaging technique during a medical procedure. As used herein, the proximal member 14 and the distal member 16 may generically refer to any two adjacent members, portions, or sections along any portion of the core member 11. In some embodiments, the connector assembly 12 includes one or more connector members 15 adapted and configured for connecting the members 14/16, and includes one or more radiopaque markers, for example radiopaque marker members 18a, 28b, and 28c, disposed adjacent the connector member 15, as discussed in more detail below. FIG. 1 shows the core member 11 and connector assembly 12 prior to a final grinding step, and FIG. 2 shows the core member 11 and connector assembly 12 after a final grinding step, which provides a generally smooth outer profile, and can provide a taper to the core member 11.

The proximal member 14 and the distal member 16 can include any suitable structure for use as members of a core member 11. The proximal member 14 and the distal member 16 can have a solid cross-section as shown, but in some embodiments, one or both can have a hollow cross-section. In yet other embodiments, the proximal member 14 and the distal member 16 can each include a combination of sections or portions having solid cross-sections and hollow cross sections.

The proximal member 14 and the distal member 16 can be made of any suitable materials for use as members of a core member 11, and can be made of the same or dissimilar materials. For example, materials such as metals, polymers, and the like can be used as material for the proximal and distal members 14/16. In some embodiments, the proximal and distal members 14/16 are made of metals or metal alloys suitable for metal joining techniques such as welding, soldering, brazing, crimping, friction fitting, adhesive bonding, and the like.

In some embodiments, the proximal member 14 may be formed of relatively stiff material. For example, a relatively stiff metal alloy, such as straightened 304v stainless steel wire, and the like, can be used. Alternatively, proximal member 14 may include a more flexible material, for example a metal or metal alloy such as a nickel-titanium alloy (for example nitinol), nickel-chromium alloy, nickel-chromium-iron alloy, cobalt alloy, or other suitable material. The word nitinol was coined by a group of researchers at the United States Naval Ordinance Laboratory (NOL) who were the first to observe the shape memory behavior of this material. The word nitinol is an acronym including the chemical symbol for nickel (Ni), the chemical symbol for titanium (Ti), and an acronym identifying the Naval Ordinance Laboratory (NOL). In general, the material used to construct proximal member 14 may be selected to be relatively stiff for pushability and torqueability, however other embodiments are contemplated.

In some embodiments, the distal member 16 may be formed of a relatively flexible material such as a straightened super elastic or linear elastic alloy, for example, nickel-titanium wire, such as nitinol. Alternatively, distal member 16 may comprise a metal or metal alloy such as stainless steel, nickel-chromium alloy, nickel-chromium-iron alloy, cobalt alloy, or other suitable material. In general, the material used to construct distal portion 16 may be selected to be relatively flexible for trackability, but other embodiments are contemplated.

In some particular embodiments, the distal section 16 is a linear elastic nickel-titanium alloy, for example, linear elastic nitinol. "Linear elastic" nickel-titanium alloys are a category of alloys that, although similar in chemistry to conventional shape memory and superelastic varieties, exhibit distinct and useful mechanical properties. By skilled applications of cold work, directional stress, and heat treatment, the wire is fabricated in such a way that it does not display a "superelastic plateau" or "flag region" in its stress/strain curve. Instead, as recoverable strain increases, the stress continues to increase in an essentially linear relationship until plastic deformation begins. In some embodiments, the linear elastic nickel-titanium alloy is an alloy that does not show any martensite/austenite phase changes that are detectable by DSC and DMTA analysis over a large temperature range. For example, in some embodiments, there is no martensite/austenite phase changes detectable by DSC and DMTA analysis in the range of about −60° C. to about 120° C. The mechanical bending properties of such material are therefore generally inert to the effect of temperature over this very broad range of temperature. In some particular embodiments, the mechanical properties of the alloy at ambient or room temperature are substantially the same as the mechanical properties at body temperature. In some embodiments, the use of the linear elastic nickel-titanium alloy for the distal portion 16 allows the guidewire to exhibit superior "pushability" around tortuous anatomy.

In some embodiments, the linear elastic nickel-titanium alloy comprises in the range of about 50 to about 60 wt. % nickel, with the remainder being essentially titanium. In some particular embodiments, the composition comprises in the range of about 54 to about 57 wt. % nickel. One example of a suitable nickel-titanium alloy is FHP-NT alloy commercially available from Furukawa Techno Material Co. of Kanagawa, Japan.

The distal end 20 of the proximal member 14 and the proximal end 22 of distal member 16 (i.e., the joined ends) are joined or connected together using the connector structure or assembly 12. In the embodiment shown in FIGS. 1 and 2, the connector member 15 is a tubular structure, such as a hypotube as shown, or a coiled wire. The connector member 15 may have an inside diameter sized appropriately to receive the ends 20/22 of the proximal portion 14 and the distal portion 16. The ends 20/22 of the proximal and distal guidewire sections 14/16 each have a reduced diameter portion that is adapted and configured to fit within the connector member 15. In some other embodiments, however, the reduced diameter portions are not used.

The connector member 15 can have an outside diameter sufficient to accommodate any final grinding or finishing procedure that may be used. In some embodiments, the final diameter of the core wire and the connector assembly 12 may be in the range of 0.010 to 0.018 inches, for example. By way of example, not limitation, the connector member 15 may have a length of about 1.0 to 3.0 inches for an overlapping portion 12 of about 0.75 to 2.5 inches.

In yet some other embodiments, the connector member can be structure or material disposed between the proximal portion 14 and the distal portion 16. For example, the connector member may comprise an adhesive, welding material, or a metal, or metal alloy disposed between proximal portion 14 and distal portion 16 that is adapted and configured to connect the proximal portion and distal portions 14/16. For example, the connector member can be a material disposed between the proximal and distal portions 14/16 that can be welded to each of the proximal and distal portions 14/16 to attach the portions 14/16 together.

The connector member 15 can include suitable material for use in attaching the proximal and distal members 14/16. Some examples of suitable materials include a metal or metal alloy, and may include radiopaque materials. Suitable metals and metal alloys include stainless steels, nickel-titanium alloys (e.g., nitinol), nickel-chromium alloys, nickel-chromium-iron alloys, cobalt alloys, nickel, or other suitable materials. Alternatively, connector member 15 may be comprised of a polymer or a metal-polymer composite, including or not including a radiopaque filler.

As set forth above, the proximal and distal members 14/16 can be made of the same or dissimilar materials. For example, in some embodiments, the proximal and distal members 14/16 are made of dissimilar materials, and the connector assembly 12, including the connector member 15 is adapted and configured to connect dissimilar materials. For specific example, in some example embodiments when the proximal portion 14 is made of a material such as stainless steel alloy and the distal portion 16 is made of a material such as a nickel-titanium alloy, the connector member 15 is particularly adapted and configured to connect these two dissimilar materials, as will be discussed in more detail below.

Some types of alloys are particularly suitable for connector member 15 for purposes of connecting a stainless steel proximal section 14 and a nickel titanium alloy distal section 16, or visa-versa. An example is a nickel-chromium-iron alloy designated UNS N06625 and is available under the trade name INCONEL 625, which advantageously welds to both stainless steels and nickel-titanium alloys. INCONEL 625 wire may be obtained from California Fine Wire Company of Grover Beach, Calif., and has the following typical composition:

| Material | Symbol | % by wgt |
| --- | --- | --- |
| Aluminum | Al | 0.140 |
| Carbon | C | 0.070 |
| Chromium | Cr | 21.900 |
| Cobalt | Co | 0.010 |
| Copper | Cu | 0.030 |
| Iron | Fe | 2.790 |
| Manganese | Mn | 0.030 |
| Molybdenum | Mo | 9.150 |
| Nickel | Ni | 62.000 |
| Niobium | Nb | 3.540 |
| Phosphorus | P | 0.005 |
| Silicon | Si | 0.230 |
| Sulfur | S | 0.009 |
| Titanium | Ti | 0.250 |
| Tantalum | Ta | 0.010 |

Another example of a suitable alloy which welds to both stainless steels and nickel-titanium alloys is available under the trade name ALLOY C276 from Fort Wayne Metals Research Products Corporation of Fort Wayne, Ind., which has the following typical composition:

| Material | Symbol | % by wgt |
| --- | --- | --- |
| Carbon | C | 0.003 |
| Chromium | Cr | 15.810 |
| Cobalt | Co | 1.310 |
| Copper | Cu | 0.100 |
| Iron | Fe | 5.730 |
| Manganese | Mn | 0.520 |
| Molybdenum | Mo | 16.010 |
| Nickel | Ni | 57.000 |
| Phosphorus | P | 0.008 |
| Silicon | Si | 0.020 |
| Sulfur | S | 0.005 |
| Tungsten | W | 3.570 |
| Vanadium | V | 0.160 |

Another example of a suitable alloy which welds to both stainless steels and nickel-titanium alloys is available under the trade name ALLOY B2 from Fort Wayne Metals Research Products Corporation of Fort Wayne, Ind., which has the following composition:

| Material | Symbol | % by wgt |
| --- | --- | --- |
| Carbon | C | 0.005 |
| Chromium | Cr | 0.450 |
| Cobalt | Co | 0.110 |
| Copper | Cu | 0.030 |
| Iron | Fe | 1.410 |
| Manganese | Mn | 0.150 |
| Molybdenum | Mo | 27.720 |
| Nickel | Ni | 70.000 |
| Phosphorus | P | 0.004 |
| Silicon | Si | 0.020 |
| Sulfur | S | 0.002 |
| Tungsten | W | 0.140 |

The joined ends of the proximal and distal members 14/16 and the connector member 15 form a connection or joint 30. The joint 30 may be an overlapping joint, an overlapping tapered joint, a butt joint as shown in FIGS. 1–2, or any other suitable joining arrangement. In some embodiments, where the flexibility characteristics of the proximal and distal members is different, the joint can form a flexibility transition region that has a relative flexibility that is between the flexibility of the proximal member 14 and the flexibility of the distal member 16. Further examples of alternative joint structures and materials for use in joining proximal and distal portions 14/16 and additional structures of some example guidewires are disclosed in co-pending U.S. patent application Ser. No. 09/972,276 titled "GUIDEWIRE WITH STIFFNESS BLENDING CONNECTION" filed Oct. 5, 2001; and co-pending U.S. patent application Ser. No. 10/086,992 titled "COMPOSITE GUIDEWIRE" filed Feb. 28, 2002, both of which are incorporated herein by reference.

As indicated above, the connection assembly 12 includes one or more marker members, for example radiopaque marker members 18a–c, that are adapted and configured to produce a relatively bright image on a fluoroscopy screen or another imaging technique during a medical procedure. This relatively bright image aids the user of a guidewire 10 in determining its location during use.

In the embodiment shown in FIGS. 1–4, the marker members 18a–c are separate members that are adapted to be disposed adjacent the connector member 15. The marker members can be generally tubular shaped members, such as hypotubes or coils, that are disposed adjacent either end of the connector member 15, as indicated by 18a and 18c, or can include a solid member, such as a wire or ribbon that is adapted to fit within the connector member 15, as indicated by 18b. One, two, or three or more such markers can be incorporated into the assembly 12.

In at least some embodiments, one or more of the markers can be described as being part of the connector assembly 12 in that the markers are positioned adjacent, for example directly adjacent, the connector member 15. In some examples, the markers are connected to or retained with the connector member 15. In some embodiments, the markers can be described as being integral with, a portion of, joined with, joined to, in direct contact with, of unitary or monolithic construction with, the connector member 15. The radiopaque marker or markers can make up all or a portion of the connector member 15. For example, a portion or all of the connector member 15 can be made of radiopaque material.

The markers 18a–c may be made of any material that provides the desired level of radiopacity for a particular use or device. Some examples of radiopaque materials include, but are not limited to, gold, platinum, palladium, tantalum, tungsten, and plastic material loaded with a radiopaque filler, or combinations, mixtures, or alloys of any of these materials. In some embodiment, the markers can be structures that are clad or filled with radiopaque material. For example, the markers may also be fabricated from precious metal clad nitinol or stainless steel wire or filled nitinol or stainless steel tubing that can be wound to form a coil.

In at least some embodiments, it is advantageous to incorporate the markers with the connector assembly to enhance ease of construction and in some embodiments, enhance the characteristics of the medical device. For example, in some embodiments, incorporating the markers with the connector assembly provides a method whereby the markers can be positioned appropriately on the core wire while maintaining a relatively smooth profile and in some cased reducing abrupt stiffness changes. In some embodiments, the markers may also provide extra structural support to guidewire proximate connector assembly.

Guidewire 10 may further comprise additional radiopaque markers, for example a marker structure such as a coil or band disposed about distal portion 16 spaced from the connector member 15.

In the embodiment shown in FIGS. 1–2, to manufacture the connection of the core member 11 of the guidewire 10, the ends 20/22 of the proximal and distal guidewire sections 14/16 may be ground to form the desired shape (e.g., a uniform diameter, a bulbous portion, a helix, a taper, etc.) to accommodate the joint, for example an overlapping joint or a but joint. In some embodiments, for example if a butt joint is to be used, such a shape need not be ground. A recess step may be ground into the proximal and distal guidewire sections 14/16 to accommodate the connector assembly 12, if desired. Additionally, the ends 20/22 of the proximal and distal guidewire section may be shaped or tapered to provide strain relief adjacent the connector assembly.

The connector assembly 12, including the connector member 15 and one of the radiopaque markers 18a and 18c, is positioned over one of the ends 20/22 of the proximal and distal guidewire sections 14/16. A radiopaque marker wire 18b is placed within the lumen of the connector member 15. The distal end 20 of the proximal portion 14 and proximal end 22 of the distal portion 16 are then positioned adjacent the radiopaque marker wire 18b in an end-to-end arrangement. The proximal and distal guidewire sections 14/16 and the connector assembly 12 may be bonded, welded (e.g., resistance or laser welded), soldered, brazed, or otherwise connected by a suitable technique depending on the material selected for each component. Alternatively, the ends 20/22 and the connector assembly 12 may be crimped together or may be sized to establish a friction fit therebetween. Because the connection may reside within a catheter lumen during use, it is preferred that a permanent connection (as opposed to a releasable connection) be used.

It is to be appreciated that various welding processes may be utilized without deviating from the spirit and scope of the present invention. Examples of welding processes which may be suitable in some applications include LASER welding, resistance welding, TIG welding, microplasma welding, electron beam, and friction or inertia welding. LASER welding equipment which may be suitable in some applications is commercially available from Unitek Miyachi of Monrovia, Calif. and Rofin-Sinar Incorporated of Plymouth, Mich. Resistance welding equipment which may be suitable in some applications is commercially available from Palomar Products Incorporated of Carlsbad, Calif. and Polaris Electronics of Olathe, Kans. TIG welding equipment which may be suitable in some applications is commercially available from Weldlogic Incorporated of Newbury Park, Calif. Microplasma welding equipment which may be suitable in some applications is commercially available from Process Welding Systems Incorporated of Smyrna, Tenn.

Once connected, the connector assembly 12, including the connector member 15 and the marker members 18a and 18c, and the proximal and distal guidewire sections 14/16 can be shaped, for example by the use of a centerless grinding technique, to provide a smooth and uniform profile across the connection, and to straighten out small misalignments between the proximal and distal guidewire sections 14/16. Other portions of the core member 11 or the guidewire 10 may be shaped, for example through grinding, to provide the desired tapers and changes in diameter.

Guidewire 10 may be shaped or tapered by any one of a number of different techniques, for example, by centerless grinding methods as indicated above. The centerless grinding technique may utilize an indexing system employing sensors (e.g., optical/reflective, magnetic) to avoid excessive grinding of the connection. In addition, the centerless grinding technique may utilize a CBN or diamond abrasive grinding wheel that is well shaped and dressed to avoid grabbing the connector during the grinding process.

Alternatively, portions of guidewire 10 may be pre-shaped by molding or other suitable techniques. In an exemplary embodiment, proximal portion 14 and distal portion 16 may be generally tubular and connector assembly 12 may include formed or ground projections on opposite ends thereof. According to this embodiment, the projections of connector assembly 12 are adapted and configured to mate with the tubular ends of proximal portion 14 and distal portion 16.

FIG. 2 is a cross sectional view of core member 11 of the guidewire 10, post-grinding. As shown in FIG. 2, the core wire 11, including the proximal and distal core wire members 14/16, and connector assembly 12, can include one or more tapered portions. The core wire 11 can be continuously tapered, can have a tapered section or a number or series of tapered sections of differing diameters, or can have a constant diameter. In some embodiments, the core wire 11 is tapered or otherwise formed to have a geometry that decreases in cross sectional area toward the distal end thereof. If tapered, the core wire 11 can include a uniform or a non-uniform transition of the sections, depending on the transition characteristics desired. For example, the core wire 11 may be linearly tapered, tapered in a curvilinear fashion, or tapered in a step-wise fashion. The angle of any such tapers can vary, depending upon the desired flexibility characteristics. The length of the taper may be selected to obtain a more (longer length) or less (shorter length) gradual transition in stiffness. Also, as indicated above, the ends 20/22 of the proximal and distal core wire members 14/16 can be tapered or otherwise shaped to provide strain relief adjacent the connector assembly 12.

Once finally shaped or ground, in some embodiments, a flexible coil tip and/or a polymer jacket tip (optionally covering connection or joint 30) or combination thereof, or other such structure may be placed on the core member 11 of the guidewire 10. Additionally, additional structure, such as radiopaque markers, safety and/or shaping wires or ribbons (coiled or uncoiled), and the like, and combinations thereof may be placed on the core member 11 of the guidewire 10. Additionally, in some embodiments, a coating, for example a lubricious (e.g., hydrophilic) or other type of coating may be applied to all or portions of the guidewire. Different coatings can be applied to different sections of the guidewire. Some examples of such coatings and materials and methods used to create such coatings can be found in U.S. Pat. Nos. 6,139,510 and 5,772,609, which are incorporated herein by reference.

FIGS. 3 and 4 illustrate two embodiments of a guidewire 10 including different outer members or assemblies that are disposed on the core member 11 of the guidewire 10. In both of these embodiments, the core wire 11 includes structure and materials similar to that shown and described in reference to FIG. 2, wherein like reference numerals indicate similar structure.

FIG. 3 shows an embodiment wherein an outer member comprises an outer polymeric sleeve 24 that is disposed around the core member 11. The sleeve 24 extends along and is attached to at least a portion of the length of the core member 11, and in the embodiment shown, extends proximally over the joint 30 and distally beyond the distal end of the core member 11. The sleeve 24 may be comprised of a material having the desired strength, flexibility or other desired characteristics. Some suitable materials include polymers, and like material. Examples of suitable polymer material include any of a broad variety of polymers generally known for use as guidewire polymer sleeves. The use of a polymer for sleeve 24 can serve several functions. The use of a polymer sleeve 24 can improve the stiffness/flexibility properties of the distal portion of the guidewire 10. The choice of polymers for the sleeve 24 will vary the flexibility. For example, polymers with a low durometer or hardness will make a very flexible or floppy tip. Conversely, polymers with a high durometer will make a tip which is stiffer. The use of polymers for the sleeve 24 can also provide a more atraumatic tip for the guide wire. An atraumatic tip is better suited for passing through fragile body passages. Finally, a polymer can act as a binder for radiopaque materials, as discussed in more detail below.

In some embodiments, the polymer material used is a thermoplastic polymer material. Some examples of some suitable materials include polyurethane, elastomeric polyamides, block polyamide/ethers (such as Pebax), silicones, and co-polymers. The sleeve 24 may be a single polymer, multiple layers, or a blend of polymers. By employing careful selection of materials and processing techniques, thermoplastic, solvent soluble and thermosetting variants of these materials can be employed to achieve the desired results.

The sleeve 24 can be disposed around and attached to the guidewire 10 using any suitable technique for the particular material used. In some embodiments, the sleeve 24 is attached by heating a sleeve of polymer material to a temperature until it is reformed around the core wire 11. In some other embodiments, the sleeve 24 can be attached using heat shrinking techniques. The sleeve 24 may be finished, for example, by a centerless grinding or other method, to provide the desired diameter and to provide a smooth outer surface. Additionally, the sleeve can be shaped or ground to form a tip 28, which, for example, can be shaped into an atraumatic shape, such as a rounded tip.

In some embodiments, the sleeve 24, or portions thereof, can include, or be doped with, radiopaque material to make the sleeve 24, or portions thereof, more visible when using certain imaging techniques, for example, fluoroscopy techniques. Any suitable radiopaque material known in the art can be used. Some examples include precious metals, tungsten, bismuth subcarbonate powder, and the like, and mixtures thereof.

Additionally, in some embodiments, a coating, for example a lubricious (e.g., hydrophilic) or other type of coating may be applied over portions or all of the sleeve 24, or other portions of the guidewire 10. Hydrophobic coatings such as fluoropolymers provide a dry lubricity which improves guide wire handling and device exchanges. Lubricious coatings improve steerability and improve lesion crossing capability. Suitable lubricious polymers are well known in the art and may include hydrophilic polymers such as polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference. In some embodiments, the more distal portion of the guidewire is coated with a hydrophilic polymer as discussed above, and the more proximal portions is coated with a fluoropolymer, such as polytetrafluroethylene (PTFE).

A structure 26, such as a safety or shaping structure, may be connected to the distal portion 16 of the core wire 11. The structure 26 can be a wire or ribbon 26 that is attached to the distal portion 16 and extends distally beyond the distal end of the distal portion 16. In some embodiments, the wire or ribbon 26 can be a fabricated or formed wire structure, for example, a coiled or wound wire or ribbon. In some other embodiments, the structure 26 can be an extension of the distal portion 16 of the core wire 11 formed, for example, by grinding and flattening to form a ribbon. In the embodiment shown in FIG. 3, the structure 26 is a generally straight ribbon that includes a portion that overlaps with and is attached to distal portion 16, and a portion that extends distally of the distal portion 16. In some embodiments, the ribbon 26 has a length in the range of about 0.8 to about 2 inches, and in some embodiments can extend about 0.2 to about 1 inch distally of the core wire 11.

The structure 26 can be made of any suitable material and sized appropriately to give the desired characteristics, such as strength and flexibility characteristics. Some examples of suitable materials include metals, metal alloys, polymers, and the like. In some embodiments, the structure 26 may be formed of a metal or metal alloy such as stainless steel, nickel-chromium alloy, nickel-chromium-iron alloy, cobalt alloy, a nickel-titanium alloy, such as a straightened super elastic or linear elastic alloy (e.g., nickel-titanium) wire. The structure 26 can be attached using any suitable attachment technique. Some examples of attachment techniques include soldering, brazing, welding, adhesive bonding, crimping, or the like. In some embodiments, the ribbon or wire 26 can function as a shaping structure or a safety structure.

FIG. 4 is a cross sectional view of guidewire 110 having an alternate outer assembly 124. According to this embodiment, outer assembly 124 comprise a coil 125 disposed along at least a portion of the length of guidewire 110. The coil 125 extends along and is attached to at least a portion of the length of the core member 11. In the embodiment shown, the coil 125 extends proximally over the joint 30. In some other embodiments, the coil 125 does not extend proximally over the joint 30. The coil 125 extends distally beyond the distal end of the core member 11. The coil 125 is attached to the core wire 11 at one or more points along the length of the core wire 11 using any suitable attachment technique, for example soldering, brazing, welding, adhesive bonding, crimping, or the like. The distal end 127 of the coil 125 is attached to the wire or ribbon 26 via a rounded tip portion 69. The rounded tip portion 69 can be made of any suitable material, for example a solder tip, a polymer tip, and the like. The wire or ribbon can have the same general structure and be made of the same materials as discussed above with regard to FIG. 3.

The coil 125 could be single or multifilar, and can be wrapped in a helical fashion by conventional winding techniques. The coil 125 may have a relatively loose or relatively tight pitch. For example, the pitch of adjacent turns of coil 125 may be tightly wrapped so that each turn touches the succeeding turn, or the pitch may be set such that coil 125 is wrapped in an open fashion such that spaces are defined between adjacent turns of coil 125. The pitch along the length of the coil can vary. For example, the pitch may be loose near the distal tip 69 to increase distal flexibility, but may be tight near the proximal portion. Outer member 124 may comprise a single layer coil, a multiple layer coil, or combinations thereof. Additionally, the pitch may be altered amongst different layers.

The coil 125 may be made of a variety of materials including metals, metal alloys, polymers, and the like. Some examples of material for use in the coil include stainless steel, nickel-chromium alloy, nickel-chromium-iron alloy, cobalt alloy, or other suitable materials. Some additional examples of suitable material include straightened super elastic or linear elastic alloy (e.g., nickel-titanium) wire, or alternatively, a polymer material, such as a high performance polymer. In some embodiments, the coil 125 can be made of a radiopaque materials such as gold, platinum, tungsten, or the like, or alloys thereof that may serve to further aid visualization of the guidewire in conjunction with connector assembly 12 (and, thus, markers 18a–c) to position guidewire 110 or make measurements during use. The coil 125 may be formed of round wire or flat ribbon ranging in dimensions to achieve the desired flexibility and other characteristics.

Refer now to FIG. 5, which shows a partial cross sectional view of a guidewire 210 including an elongated core member 211. The core member 211 includes an elongated proximal portion or member 214, an elongated distal portion or member 216 and a connector structure or assembly 212 including structure adapted and configured for connecting the proximal member 214 and the distal member 216. The connector assembly 212 includes one or more connector member 215 adapted and configured for connecting the members 214/216, and includes one or more radiopaque marker members 218a, and 218b. The core member 211 including proximal and distal portions 214/216, connector structure 212, connector member 215, and radiopaque marker members 218a and 218b can have the same general structure and be made of the same materials as discussed above with regard to the embodiments shown in FIGS. 1–4.

The connector structure or assembly 212 in the embodiment shown in FIG. 5 is similar to that shown in FIGS. 1–4, but rather than a butt joint, an overlapping joint configuration 230 is used. The ends 220/222 of the proximal and distal guidewire sections 214/216 each have a first reduced diameter portion 231 and 233 that is adapted and configured to fit within the connector member 215, and each have a second reduced diameter portion 235 and 237 that are adapted and configured to overlap each other. The connector member 215 is a tubular structure, such as a hypotube as shown, or a coiled wire. The connector member 215 has an inside diameter sized appropriately to receive the ends 220/222 of the proximal portion 214 and the distal portion 216. The radiopaque marker members 218a and 218b are generally tubular shaped members, such as hypotubes or coils, that are disposed adjacent either end of the connector member 215, as indicated by 218a and 218b. The connection between the proximal and distal guidewire sections 214/216 and the connector assembly 212 may be achieved using the same techniques and materials as discussed above with regard to the embodiments shown in FIGS. 1–4.

The guidewire 210 also includes an outer distal assembly 224 that includes a combination of a sleeve 223 and a coil 225 disposed about a portion of the core wire 211. The sleeve 223 extends over a portion of the distal guidewire section 216, and has a proximal end that terminates distally of the connection or joint 230. The distal end of the sleeve 223 ends proximally of the distal end of the distal guidewire section 216. In other embodiments, the sleeve 223 can extend further in a proximal direction, and in some cases can extend over the connection 230 and/or over a portion of the proximal guidewire section 214. In yet other embodiments, the sleeve 223 can extend further distally, for example, extend distally beyond the distal end of the distal guidewire section 16. The sleeve 223 can be made of and include the same materials, structure, radiopaque loading, and coatings, and be made in accordance with the same methods as discussed above with regard to the embodiment shown in FIG. 3.

The coil 225 extends from adjacent the distal end of the sleeve 223 to beyond the distal most portion of the ribbon 226. The coil 225 is attached at one or more points to the distal guidewire section 216 using any suitable attachment technique, for example soldering, brazing, welding, adhesive bonding, crimping, or the like. The distal end 227 of the coil 225 extends distally beyond the distal end of the core member 211, and is attached to the ribbon 226 via a rounded tip portion 269. The rounded tip portion 269 can be made of any suitable material, for example a solder tip, a polymer tip, and the like. The wire or ribbon 226 can have the same general structure and be made of the same materials as discussed above with regard to FIG. 3. Additionally, the coil 225 may be made of the materials and include structure as described above in reference to the embodiment of FIG. 4.

Refer now to FIG. 6, which shows a partial cross sectional view of guidewire 210 including structure very similar to that shown in FIG. 5, wherein like reference numerals indicate similar structure. The guidewire 210 includes an elongated core member 211 having proximal and distal portions 214/216, and a connector assembly 212 for connecting the proximal and distal portions 214/216. The connector assembly 212 includes connector member 215, and radiopaque marker members 218a and 218b. An overlapping joint configuration 230 is used, as in FIG. 5. In the embodiment shown in FIG. 6, however, an outer assembly 224 comprises a polymer sleeve 223, and does not include a coil portion. The sleeve 223 can be similar to that shown in the embodiment of FIG. 3, but does not extend proximally over the joint 230. Additionally, in the embodiment of FIG. 6, the sleeve includes a distal portion 270 and a proximal portion 271, wherein the distal and proximal portions 270/271 include different levels of radiopaque material. For example, the distal portion 270 can include or be doped with, a higher amount of radiopaque material than the proximal portion 271.

Refer now to FIG. 7, which shows a partial cross sectional view of guidewire 310 including an elongated core member 311. The core member 311 includes an elongated proximal portion or member 314, an elongated distal portion or member 316 and a connector structure or assembly 312 including structure adapted and configured for connecting the proximal and distal members 314/316. The connector assembly 312 includes one or more connector member 315 adapted and configured for connecting the members 314/

316, and includes one or more radiopaque marker members 318a and 318b. The core member 311 including proximal and distal portions 314/316, connector structure 312, connector member 315, and radiopaque marker members 318a and 318b can have the same general structure and be made of the same materials as discussed above with regard to the embodiments shown in FIGS. 1–6.

The connector structure or assembly 312 in the embodiment shown in FIG. 7 is similar to that shown in FIGS. 1–6, but rather than a butt joint, or a straight overlapping joint configuration, an overlapping tapered joint configuration 330 is used. The ends 320/322 of the proximal and distal guidewire sections 314/316 each have a first reduced diameter portion 331 and 333 that is adapted and configured to fit within the connector member 315, and each also have a tapered reduced diameter portion 335 and 337 that are tapered such that they are adapted and configured to overlap each other. The connector member 315 is a tubular structure, such as a hypotube as shown, or a coiled wire. The connector member 315 has an inside diameter sized appropriately to receive the ends 320/322 of the proximal and distal portions 314/316. The radiopaque marker members 318a and 318b are generally tubular shaped members, such as hypotubes or coils, that are disposed adjacent either end of the connector member 315. The connection between the proximal and distal guidewire sections 314/316 and the connector assembly 312 may be achieved using the same techniques and materials as discussed above with regard to the embodiments shown in FIGS. 1–4.

The guidewire 310 also includes an outer distal assembly 324 that includes a sleeve 323 and a safety and/or shaping structure 326, both of which can be similar in structure and material to those described above in relation to the embodiment of FIGS. 3 and 6. In the embodiment of FIG. 7, the sleeve 323 does not extend over the joint 330.

Refer now to FIG. 8, which shows a partial cross sectional view of guidewire 310 including structure very similar to that shown in FIG. 7, wherein like reference numerals indicate similar structure. However, in the embodiment of FIG. 8, the outer distal assembly 324 includes a coiled safety and/or shaping structure 326. The coiled safety and/or shaping structure 326, for example a coiled ribbon, a coiled wire, or other such coiled structure, is disposed about a portion of the core wire 311. In the embodiment shown, the coiled structure 326 is a coiled ribbon that overlaps with or surrounds a portion of the distal guidewire portion 316, and extends distally from the distal end of the core wire 311.

The coil 326 can be made of any suitable material and sized appropriately to give the desired characteristics, such as strength and flexibility characteristics. In some embodiments, the attachment of the coil 326 to the core wire 311 can also influence the characteristics of the portion of the core wire 311 overlapped by the coil 326.

Some examples of material for use in the coil 326 include stainless steel, nickel-chromium alloy, nickel-chromium-iron alloy, cobalt alloy, nickel-titanium alloy, or other suitable materials. Some additional examples of suitable material include straightened super elastic or linear elastic alloy (e.g., nickel-titanium), or alternatively, a polymer material, such as a high performance polymer. In some embodiments, the coil 326 can be made of a radiopaque materials such as gold, platinum, tungsten, or the like, or alloys thereof. The coil 326 may be formed of round or flat ribbon ranging in dimensions to achieve the desired flexibility. In some embodiments, the coil 326 may be a round wire in the range of about 0.001–0.015 inches in diameter. In some other embodiments, the coil can be made of a flat or rectangular shaped ribbon having a width in the range of about 0.002 to 0.02 inches and a thickness in the range of about 0.0005 to about 0.02 inches.

The coil 326 can be attached to the core wire 311 using any suitable attachment technique. Some examples of attachment techniques include soldering, brazing, welding, adhesive bonding, crimping, or the like. In the embodiment shown, the coil 326 is attached at two attachment points 364 and 365.

The coil 326 is wrapped in a helical fashion by conventional winding techniques. The pitch of adjacent turns of coil 326 may be tightly wrapped so that each turn touches the succeeding turn or the pitch may be set such that coil 326 is wrapped in an open fashion. In some embodiments, the coil can have a pitch of up to about 0.4 inches, in some embodiments a pitch of up to about 0.08 inches, and in some embodiments, a pitch in the range of about 0.01 to about 0.08 inches. The pitch can be constant throughout the length of the coil 326, or can vary, depending upon the desired characteristics, for example flexibility. In some embodiments, the pitch of the coil 326 portion that overlaps with the core wire 311 is smaller, while the pitch of the coil portion that does not overlap with the core wire is larger. For example, in some embodiments, the pitch of the coil portion that overlaps with the core wire 311 is in the range of 0.01 to 0.08 inches, for example 0.04 inches, while the pitch of the coil portion that does not overlap with the core wire 311 is up to about 0.08 inches. These changes in coil pitch can be achieved during the initial winding of the wire, or can be achieved by manipulating the coil 326 after winding or after attachment to the guidewire. For example, in some embodiments, after attachment of the coil 326 to the guidewire 311, a larger pitch can be achieved on the distal portion of the coil 326 by simply pulling the coil.

The diameter of the coil 326 is preferably sized to fit around and mate with the distal portion of the core wire 311, and to give the desired characteristics. The diameter of the coil 326 can be constant or tapered. In some embodiments, the coil 326 is tapered to mate with tapered sections of the core wire 311. The diameter of the coil 326 can also include a taper beyond the distal end of the core wire 326, as desired.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A medical device comprising:
    a first elongated member having a proximal portion and a distal portion;
    a second elongated member having a proximal portion and a distal portion;
    wherein the first elongated member comprises a first material and the second elongated member comprises a second material different from the first material;
    wherein the second material comprises a nickel-titanium alloy;
    a tubular connector disposed adjacent the distal portion of the first elongated member and adjacent the proximal portion of the second elongated member to connect the first and second elongated members, wherein the connector has a proximal-most end and a distal-most end; and
    one or more non-coiled radiopaque marker bands disposed adjacent the connector for imaging the device, wherein at least one of the one or more non-coiled radiopaque marker bands contacts either the proximal-most end or the distal-most end of the connector.

2. The medical device of claim 1, wherein the connector is disposed about the distal portion of the first elongated member and about the proximal portion of the second elongated member.

3. The medical device of claim 1, wherein at least one of the one or more non-coiled radiopaque marker bands is disposed about the distal portion of the first elongated member adjacent the connector.

4. The medical device of claim 1, wherein at least one of the one or more non-coiled radiopaque marker bands is disposed about the proximal portion of the second elongated member adjacent the connector.

5. The medical device of claim 1, wherein the device is a guidewire.

6. The medical device of claim 1, wherein the first material comprises a stainless steel alloy.

7. The medical device of claim 1, wherein two non-coiled radiopaque marker bands are disposed adjacent the connector for imaging the device.

8. The medical device of claim 7, further comprising a third radiopaque marker disposed adjacent the connector for imaging the device.

9. The medical device of claim 8, wherein the connector is disposed about the distal portion of the first elongated member and about the proximal portion of the second elongated member, and wherein the third radiopaque marker is disposed within the tubular connector between the distal portion of the first elongated member and the proximal portion of the second elongated member.

10. A medical device, comprising:
a first elongated member having a proximal portion and a distal portion;
a second elongated member having a proximal portion and a distal portion;
wherein the first elongated member comprises a stainless steel alloy, and the second elongated member comprises a nickel-titanium alloy; and
a tubular connector assembly including a non-coiled radiopaque marker band that is in contact with either a proximal-most end or a distal-most end of the connector assembly, the connector assembly disposed adjacent the distal portion of the first elongated member and adjacent the proximal portion of the second elongate member to connect the first and second elongated members.

11. The medical device of claim 10, wherein the connector assembly includes a connector member that is disposed about the distal portion of the first elongated member and about the proximal portion of the second elongated member, and a second radiopaque marker is disposed within the connector member.

12. The medical device of claim 10, wherein the connector assembly includes a connector member that is disposed about the distal portion of the first elongated member and about the proximal portion of the second elongated member, and the non-coiled radiopaque marker band is disposed adjacent the connector member about either the distal portion of the first elongated member or about the proximal portion of the second elongated member.

13. The medical device of claim 10, wherein the connector assembly further comprises a second radiopaque marker.

14. The medical device of claim 10, wherein the connector assembly further comprises a second and a third radiopaque marker.

15. The medical device of claim 10, wherein the device is a guidewire.

16. The medical device of claim 10, wherein the connector assembly is disposed about the distal portion of the first elongated member and about the proximal portion of the second elongated member.

17. The medical device of claim 16, wherein the non-coiled radiopaque marker band is disposed about either the distal portion of the first elongated member adjacent the tubular connector assembly or about the proximal portion of the second elongated member adjacent the tubular connector assembly.

18. A method of manufacturing a medical device, the method comprising:
providing a first elongate member and a second elongate member, each having a proximal pardon and a distal portion;
wherein the first elongate member comprises a fast material and the second elongate member comprises a second material different from the first material;
wherein the second material comprises a nickel-titanium alloy;
providing a connector assembly comprising a tubular connector member and one or more non-coiled radiopaque marker bands disposed & either a proximal-most end of the tubular connector member or a distal-most end of the tubular connector member; and
connecting the distal end of the first member and the proximal end of the second member using the connector assembly.

19. The method of claim 18, wherein the connecting step includes disposing the connector member about the distal portion of the first elongate member and about the proximal portion of the second elongate member.

20. The method of claim 19, wherein at least one of the one or more non-coiled radiopaque marker bands is disposed about either the distal portion of the first elongate member or is disposed about the proximal portion of the second elongate member.

21. The method of claim 18, wherein the connector assembly includes two non-coiled radiopaque marker bands.

22. The method of claim 21, wherein the connector assembly further comprises a third radiopaque marker disposed adjacent the tubular connector member.

23. The method of claim 18, wherein the device is a guidewire.

24. The method of claim 18, wherein the first material comprises a stainless steel alloy.

25. A medical device, comprising:
a first elongated member having a proximal portion and a distal portion;
a second elongated member having a proximal portion and a distal portion;
a tubular connector assembly including a non-coiled radiopaque marker band that is in contact with either a proximal-most end or a distal-most end of the connector assembly, the connector assembly disposed adjacent the distal portion of the first elongated member and adjacent the proximal portion of the second elongate member to connect the first and second elongated members;
wherein the connector assembly is disposed about the distal portion of the first elongated member and about the proximal portion of the second elongated member; and
a second radiopaque marker is disposed within the tubular connector assembly.

26. A method of manufacturing a medical device, the method comprising:

provinding a first elongate and a second elongate member, each having a proximal portion and a distal portion;

providing a connector assembly comprising a tubular connector member and one or more non-coiled radiopaque marker member;

disposing the non-coiled radiopaque marker member within the tubular connector member;

connecting the distal end of the first member and the proximal end of the second member using the connector assembly; and wherein the connecting step includes disposing the connector member about the distal portion of the first elongate member and about the proximal portion of the second elongate member.

27. A method of manufacturing a medical device, the method comprising:

providing a first elongate member and a second elongate member each having a proximal portion and a distal portion;

providing a connector assembly comprising a tubular connector member and one or more non-coiled radiopaque marker bands disposed at either a proximal-most end of the tubular connector member or a distal-most end of the tubular connector member; and connecting the distal end of the first member and the proximal end of the second member using the connector assembly by laser welding the first and second elongate members to the connector member.

28. A method of manufacturing a medical device comprising:

providing a first elongate member comprising a nickel-titanium alloy and a second elongate member comprising a metallic material different from the nickel-titanium alloy, each having a proximal end and a distal end;

providing a tubular connector member and one or more non-coiled radiopaque marker bands;

connecting the distal end of the first member and the proximal end of the second member using the tubular connector member, the tubular connector member including a proximal-most end and a distal-most end; and disposing the one or more non-coiled radiopaque marker bands adjacent the tubular connector member, wherein at least one of the one or more non-coiled radiopaque marker bands contacts either the proximal-most end or the distal-most end of the tubular connector member.

29. A medical device comprising:

a first elongated member comprising a nickel-titanium alloy;

a second elongated member comprising a stainless steel alloy;

a tubular connector adapted and configured to connect the first and second elongated members, the tubular connector including a proximal-most end and a distal-most end; and a non-coiled radiopaque marker band disposed adjacent the tubular connector and in contact with either the proximal-most end or the distal-most end of the tubular connector.

* * * * *

UNITED STATES PATENT AND TRADEMARK OFFICE
CERTIFICATE OF CORRECTION

PATENT NO. : 7,153,277 B2  
APPLICATION NO. : 10/309306  
DATED : December 26, 2006  
INVENTOR(S) : Peter Skujins et al.

Page 1 of 1

It is certified that error appears in the above-identified patent and that said Letters Patent is hereby corrected as shown below:

Column 2  
Line 58, delete "28b", and insert therefor --18b--.

Line 58, delete "28c", and insert therefor --18c--.

Column 16  
Line 16, delete "pardon", and insert therefor --portion--.

Line 18, delete "fast", and insert therefor --first--.

Line 25, delete "&", and insert therefor --at--.

Column 17  
Line 3, after "first elongate" and before "and a second," insert --member--.

Signed and Sealed this

Thirteenth Day of March, 2007

JON W. DUDAS  
*Director of the United States Patent and Trademark Office*